United States Patent [19]

Ebert et al.

[11] Patent Number: 5,507,412

[45] Date of Patent: Apr. 16, 1996

[54] CENTRALIZED MULTICHANNEL FLUID DELIVERY SYSTEM

[75] Inventors: Holger Ebert, Nürnberg; Bernt Klinger, Lübeck; Matthias Heimermann, Wolfenbüttel; Uvo Hölscher, Stockelsdorf, all of Germany

[73] Assignee: Drägerwerk AG, Lübeck, Germany

[21] Appl. No.: 259,467

[22] Filed: Jun. 14, 1994

[30] Foreign Application Priority Data

Jun. 19, 1993 [DE] Germany ............ 43 20 365.5

[51] Int. Cl.⁶ .................................................. B67D 5/08
[52] U.S. Cl. .................... 222/63; 222/134; 222/135; 604/67
[58] Field of Search .................... 222/134, 63, 135, 222/145.7, 333, 23; 128/DIG. 13; 604/65, 67, 154

[56] References Cited

U.S. PATENT DOCUMENTS

| | | | |
|---|---|---|---|
| 4,341,327 | 7/1982 | Zeitz | 222/145.7 X |
| 4,653,010 | 3/1987 | Figler et al. | 222/134 X |
| 4,756,706 | 7/1988 | Kerns et al. | |
| 4,908,017 | 3/1990 | Howson et al. | 604/67 |
| 4,919,596 | 4/1990 | Slate et al. | 604/154 X |
| 5,207,642 | 5/1993 | Orkin et al. | 604/65 |

FOREIGN PATENT DOCUMENTS

| | | |
|---|---|---|
| 0319268A2 | 11/1988 | European Pat. Off. . |
| 3027523 | 6/1992 | European Pat. Off. . |
| 332997 | 3/1985 | Germany . |

*Primary Examiner*—Gregory L. Huson
*Attorney, Agent, or Firm*—McGlew and Tuttle

[57] ABSTRACT

A multichannel metering system, for metering preselected fluid flows from individual fluid flow sources, includes a control device, and data fields which are located in the control device (memory) and describe at least the metering of the individual fluid flows, and can be polled to an operating surface connected to the control device with a data input circuit and with a data output circuit. The data field associated with a fluid flow source can be selected in a simple manner using selector switches associated as part of the data input circuit with individual fluid flow sources by which selector switches at least segments of the fluid flow source belonging to the fluid flow source selected can be represented on the operating surface. At least part of the data input circuit are switched into functional connection with the data field belonging to the fluid flow source selected.

20 Claims, 4 Drawing Sheets

CENTRALIZED MULTICHANNEL FLUID DELIVERY SYSTEM

FIELD OF THE INVENTION

The present invention pertains to a multichannel metering system for metering preselected fluid flows from individual fluid flow sources via separate discharge lines, which receive the fluid flows, with adjusting means, which are associated with the fluid flow sources, to influence the fluid flows which are coupled with a programmable control device, and with data fields, which are stored in the control device. The data fields describe at least the metering of the individual fluid flows, and can be polled to an operating surface with a data input circuit and a data output circuit which operating surface is connected to the control device.

BACKGROUND OF THE INVENTION

A multichannel metering system of this type has become known from EP-B 302,752. In the prior-art metering system, a plurality of infusion containers acting as fluid flow sources are fastened to a chassis. These flow sources are connected to individual discharge lines, through which the substances or fluid flows to be metered reach a collection line, in which the individual fluid flows unite. A flow-adjusting means, with which each fluid flow can be individually influenced, is located in the line path of each discharge line. The flow-adjusting means are connected to a central, programmable control device, which is located in the lower part of the chassis, and which permits the selective actuation of the individual flow-adjusting means. The control device has a means for storing information, in which data fields on discharge schedules of the individual types of fluids are stored. The data fields can be polled in the form of menu screens to an operating surface, which has as the output means a "touch screen" for displaying the individual menu screens or menu masks, and has a "light pen" as an input means, with which individual menu functions can be activated via the touch screen. The individual flow-adjusting means for the fluid flows can be set to select metering rates by means of the menu screens, on the one hand, and, on the other hand, it is possible to specify information on the compatibility of individual types of fluids, and it is possible, via a keyboard menu screen, to read alphanumeric data, e.g., general patient data or metering rates, into the control device.

The prior-art metering system is highly complex in terms of operation, because defined menu screens must be polled one after another to perform defined control and monitoring functions, observing an operation hierarchy. A spontaneous, direct access to the data field of a defined fluid flow is not possible.

DE-A 33,29,977 discloses a four-channel metering system, in which the metering rates of the individual fluid flows are monitored by a central control device, but an individual coding switch, with which the metering rate can be set manually, is associated with each fluid flow source. All coding switches are connected to the control device, which calculates a total rate of delivery from the individual metering rates delivered by the coding switches to the control device, and displays it via a display on the control device.

The disadvantage of the prior-art metering system is the fact that corresponding coding switches must be provided for the individual metering rates at each fluid flow source because of the decentralized data input, as a result of which the coding switches may be located in a field of view that is unfavorable for the user, and there is a great risk of incorrect setting.

SUMMARY AND OBJECTS OF THE INVENTION

The basic task of the present invention is to improve a multichannel metering system such that essential operating functions are integrated on a central operating surface, on the one hand, and, on the other hand, the data fields associated with the individual fluid flow sources can be polled in a simple manner, and the risk of confusion of the fluids to be metered is reduced.

This object is attained in that individual fluid flow sources and/or predetermined groups of fluid flow sources are associated with selector switches, which are part of the data input circuit, and by which at least segments of the data fields belonging to the fluid flow source selected or of the data fields belonging to the selected group of fluid flow sources can be represented on the operating surface, and by which at least parts of the data input circuit are brought into functional connection with the data field belonging to the fluid flow source selected or with the data fields belonging to the selected group of fluid flow sources.

The advantage of the present invention is essentially the fact that direct access to the data field of a fluid flow source or to the data fields of a predetermined group of fluid flow sources is possible by means of the selector switches. The number of fluid flow sources connected to the multichannel metering system may reach up to twenty, and they operate either simultaneously or according to a fixed priority sequence. The manner of association of the selector switches either to individual fluid flow sources or to individual groups of fluid flow sources is determined by the total number of fluid flow sources connected to the metering system. If up to circa six fluid flow sources are present, one selector switch is associated, in general, with each fluid flow source, and a division into groups is performed above this limit, and the upper limit is approximately six fluid flow sources in each group.

When the data field of a defined fluid flow source is selected by means of one of the selector switches, the functional connection between the data input circuit and the data field can be established such that a direct access to setting parameters of the selected fluid flow is possible. Thus, the metering rate belonging to the fluid flow can be read, e.g., directly on the operating surface, and it can also be changed there if necessary. In the simplest case, the selector switch is a key, which provides the user on operation with a tactile feedback, indicating that the preselected fluid flow is activated on the operating surface.

The data input and data output are performed via the operating surface, which has a data output circuit and a data input circuit for this purpose. The data input circuit may be designed in the form of discrete keys, with which command information can be entered into the control device. To enter analog variables, e.g., the metering rate, it is advantageous to provide a continuously variable adjusting member with an acknowledge key, e.g., a turning knob with an angle transmitter and a push contact as an acknowledge key. The data output circuit is an LC display in the simplest case.

The selector switches are advantageously arranged directly at the fluid flow sources and/or the adjusting means. It is achieved as a result that the user must first consciously select a defined fluid flow source by actuating the selector switch before an adjustment of the metering rate via the operating surface is possible. If the fluid flow source is designed as, e.g., a syringe and the adjusting means is a motor drive actuating the plunger of the syringe, the selector switch is advantageously arranged on the syringe or the motor drive.

It is advantageous to provide the selector switches with an indicator means indicating the tactile actuation of the switches, which may be designed as, e.g., a photodiode, which is arranged within the keyboard and lights up when the selector switch is depressed. The user thus receives direct feedback, indicating that the data field belonging to the selected fluid flow source on the operating surface is activated. As an alternative or in addition to the optical display, an acoustic signal transmitter may be present as well. One display unit, with which a predetermined parameter of the fluid flow is displayed for the user, is advantageously associated with each of the selector switches. The fluid flow parameter displayed may be, e.g., the metering rate in mL per hour, which belongs to the fluid flow in question.

In an advantageous embodiment of the present invention, a manual operating switch is provided, by which predetermined adjusting means can be brought into the switched-off position such that the metering of the fluid flow can be influenced manually. When the manual operating switch is actuated, the control device generates a control command, by which the predetermined adjusting means is switched into the switched-off position. If the manual operating switch was actuated in conjunction with a selector switch, only the adjusting means belonging to the selector switch is switched to manual operation. The switching over into the switched-off position can be achieved as follows: If the adjusting means is designed as, e.g., a self-locking motor drive with a clutch, the flux of force between the drive and the fluid flow source is abolished by the control command by actuation of the clutch. If the adjusting means consists of a non-self-locking drive with a brake, the brake is unlocked with the control command.

In an advantageous embodiment of the present invention, a reflux barrier, with which the fluid is prevented from flowing back from the discharge line into the fluid flow source, is in operation at least in the switched-off position of the adjusting means. The reflux barrier may be designed as, e.g., a directional valve.

In an advantageous embodiment of the present invention, flow-measuring means are provided to monitor the fluid flows metered into the individual discharge lines, e.g., during manual operation, and the said flow-measuring means send a flow-proportional measured quantity to the control device, and the said measured quantity is compared with stored limit values there. If necessary, the control device generates a warning signal, which is displayed on the operating surface. If the metering of the fluid flow is to be switched over to manual operation, manual metering can be blocked by the control device when the limit value is exceeded or not met. A reflux barrier can thus be obtained as well. The flow-measuring means may either be coupled with the adjusting means or be arranged downstream of the fluid flow sources as independent units. For example, a flow-measuring means and an adjusting means are coupled when the fluid flow source is designed as a syringe and the adjusting means is designed as a motor drive actuating the plunger of the syringe, and the flow-measuring means measures the displacement of the syringe plunger. If the flow-measuring means is designed as a component measuring the liquid volume being delivered, it is preferably arranged in the path of a discharge line.

Provisions are made in an advantageous embodiment of the present invention to structure the data field pollable onto the data output circuit into individual, so-called primary segments and secondary segments, which are associated with the fluid flow sources, in which case only the secondary segments are brought into functional connection with the data input circuit via the selector switches, i.e., they can be changed by means of the data input circuit, in the case of a change in the status of segments of the data field. The primary segments of the data field are, e.g., the type and the design of the fluid flow source, the specification of the solution to be metered, the test subject's body weight, and the metering rate of the solution to be metered relative to the test subject's body weight as a weight-based dose. The secondary element of the data field may be, e.g., the metering rate belonging to the weight-based dose in volume per unit of time, or a metering to be set anew by the user.

In an advantageous embodiment of the present invention, at least some of the primary segments and secondary segments belonging to one fluid flow source are arranged in a display line or display column on the data output circuit. For greater clarity, it is advisable to arrange parts of primary segments and secondary segments which directly correspond to one another, e.g., the weight-based dose and the metering rate, directly one on top of another or next to one another in the display. In those cases in which a given secondary segment requires much space for display, an adjacent secondary segment can be briefly written over. The primary segments are excepted from the possibility of overwriting.

A reference field, which supports the representation of the change in status of at least one secondary segment, which has been brought into functional connection with the data input circuit, is advantageously provided on the data output circuit. This secondary segment may be, e.g., a metering rate of a fluid flow, which is to be changed, the previous metering rate being indicated in the left-hand part of the reference field, and the new metering rate in the right-hand part. Additional information may also be displayed in the reference field, e.g., to check and confirm a newly set metering rate.

Provisions are made in an advantageous embodiment of the present invention to establish the status of predetermined primary segments in a restrictedly guided operating sequence, which is influenced by the control device. This restrictedly guided operating sequence runs, e.g., when fluid flow sources are to be newly included in the metering system, and the specification of the fluid flow source, of the solution to be metered, and the metering parameters, e.g., the metering rate, are to be entered in the control device via the data input device, so that no metering can be started without complete information having been polled by the user.

Display units, which are separately associated with the individual fluid flow sources, and by which a predetermined actual value of the fluid flow being metered from the fluid flow source in question is displayed, are advantageously provided in a predetermined group of fluid flow sources of a multichannel metering system. The predetermined actual value may be the fluid flow volume measured by the flow-measuring means, with which the fluid volume actually metered is displayed for the user directly at each fluid flow source, and the value displayed can thus be brought into connection with the corresponding fluid flow source also visually. Interruptions in fluid flow metering can also be read directly from the display units.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DETAILED DESCRIPTION OF THE PREFERRED EMBODIMENT

Figure 1:
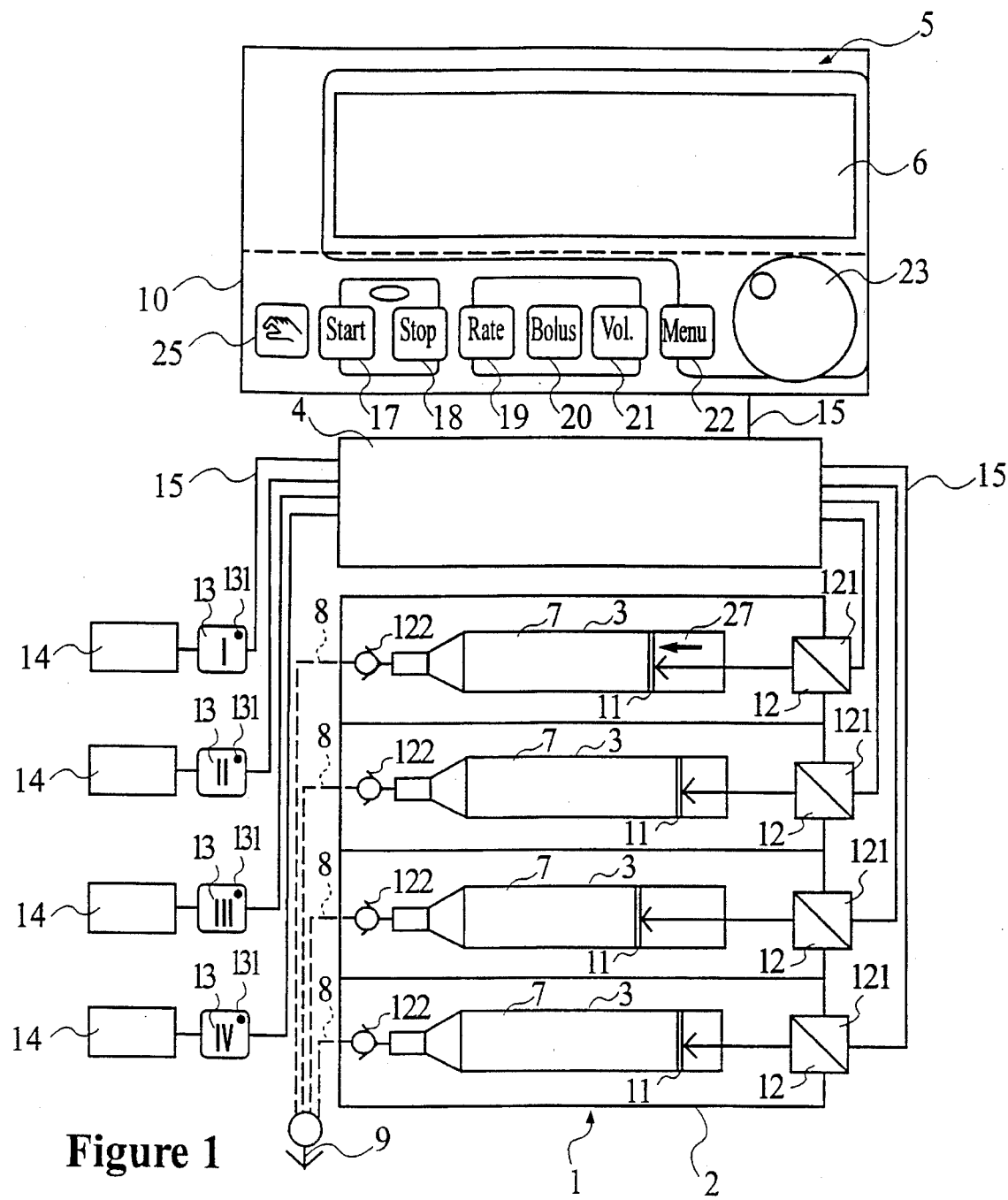
FIG. 1 is a schematic view showing a design of a four-channel infusion system.

The four-channel metering system 1 represented in FIG. 1 is comprised of a syringe holder 2 for four metering syringes 3, a control device 4, and a first operating surface 5 with a data input 10 and with an LC display 6 as a data output. The metering syringes, hereinafter called the syringes 3, are filled with solutions 7 as fluids, which flow into a collection line 9 via respective reflux barriers 122 and discharge lines 8. The syringes are used as fluid flow sources for metering preselected fluid flows, i.e., the solutions 7. The metering of the solutions 7 is performed by means of syringe plungers 11 located in the syringes 3, which can be actuated by a motor drive 12 acting as an adjusting means to perform stroke movements. The liquid volume being metered is determined by means of flow-measuring means 121, which record the displacement of the syringe plungers 11. Selector switches 13, with which the individual syringes 3 can be selected, and a display unit 14, which displays the metering rate actually set, are located next to each of the syringes 3. The motor drives 12, the first operating surface 5, the flow-measuring means 121, the selector switches 13, and the display units 14 are connected to the control device 4 via control lines 15. The control device 4 has a means for storing information, in which data fields on metering schedules of a plurality of solutions to be metered, which data fields are not represented in FIG. 1, are stored, as well as a programming means, which is likewise not shown, with which control and monitoring functions can be performed. The data fields associated with the individual solutions contain, e.g., the exact designation of the solution, the type of the syringe, and the metering rate.

The data input 10 is used to enter control commands into the control device 4, and it is formed of keys for metering start 17, metering stop 18 metering rate 19, bolus 20, metering volume 21, menu 22, and manual operation 25, as well as of an analog adjusting member 23 with integrated acknowledge key, which is actuated by depressing the adjusting member 23. The metering system 1 is operated by the interaction of the selector switches 13 with the keys 17 through 22 and with the adjusting member 23. A specific channel, i.e., a defined solution 7, can be selected with the selector switches 13, and defined settings within this selected channel can then be performed or edited via the data input circuit 10. The individual channels are marked by Roman numerals I through IV on the selector switches 13. The selector switches are provided with photodiodes 131, which, acting as indicator means, give an optical feedback of the switch operation.

Figure 2:
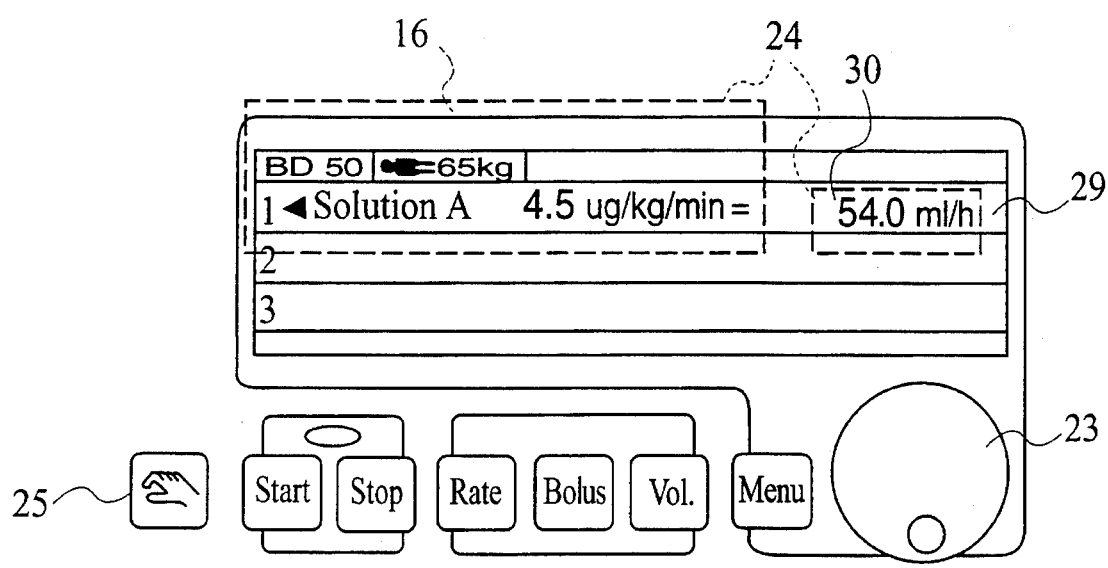
FIG. 2 is an example of a data field displayed on the LC display.

FIG. 2 shows an example of a data field 24 displayed on the LC display (output) 6 for setting or editing a metering rate of the solution 7 to be metered (FIG. 1) in channel I.

The type of syringe placed into the syringe holder 2 (FIG. 1) was a model "BD 50" syringe 3 containing the solution 7. The test subject has a body weight of 65 kg.

The data field 24 represented in FIG. 2 is divided into so-called primary segments 16 and secondary segments 30. The primary segments 16 are composed here of the following individual segments: Syringe model "BD 50" body weight "65 kg" channel identification "I" specification of the solution "solution A," and the weight-based dose of 4.5 µg/kg/minute, which is related to the body weight. The triangular symbol next to the channel identification 'I' to the right shows the state of delivery: "Metering."

Figure 3:
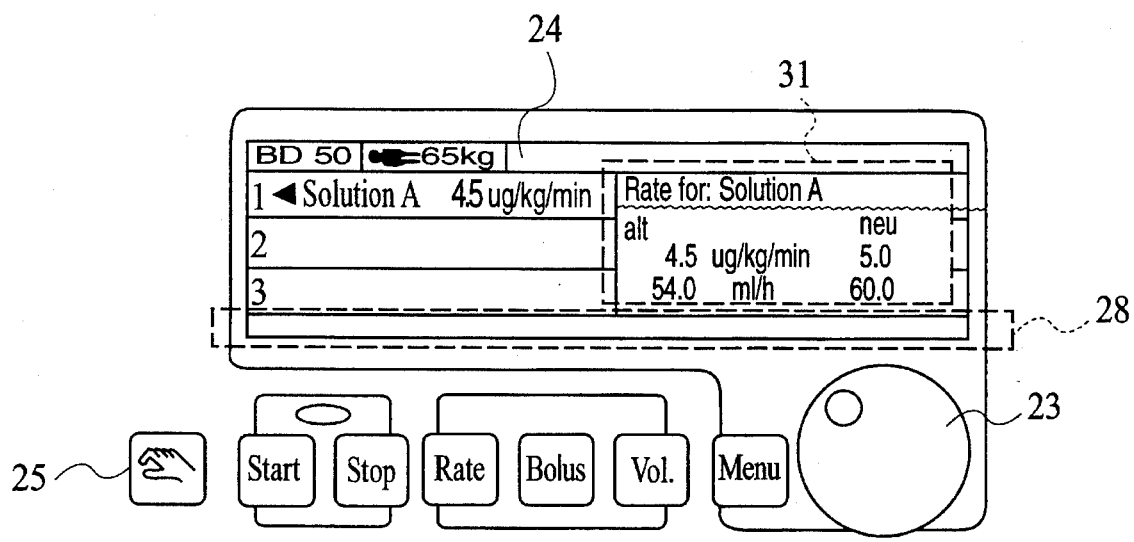
FIG. 3 is an example of a data field displayed via the LC display during a change in the metering rate.

The secondary segment 30 indicates the metering rate "54.0 mL/hour," and the corresponding segments (weight-based dose and metering rate) are arranged in a display line 29 next to each other. If the metering rate is now to be changed or edited in channel "I," channel I is selected by depressing the selector switch 13 (FIG. 1) belonging to channel I, this places the control device 4 in meter management mode for channel I and the metering rate displayed in the secondary segment 30 is then increased or decreased by means of the adjusting member 23 by turning it to the right or the left. When channel I is selected, a new secondary segment 31 overwrites the secondary segment 30, as is illustrated in FIG. 3. The new secondary segment 31 extends over three display lines 29 and contains juxtaposed the old metering rate and the new metering rate of 5.0 µg/kg/minute. The new metering rate is acknowledged by depressing the adjusting member 23 wherein it is read into the control device 4. A reference line 28 of the data field 24 prompts checking and confirmation of the rate setting, which had happened by the prior depression of the adjusting member 23.

The operating sequence of the metering system at start-up will be explained on the basis of an example. After inserting and locking the syringe 3 in channel I, the primary data segment 16 (FIGS. 1 and 2) of the channel I is automatically activated, and a restrictedly guided operating sequence, which takes place in the following manner, is triggered by the control device 4. The user is prompted via the LC display 6 to first identify the type of the syringe inserted. A list of possible types of syringes is displayed for this purpose, after which the type of syringe inserted is selected by means of the adjusting member 23 and acknowledged by depressing the adjusting member 23. The solution 7 contained in the syringe 3 is selected in the same manner. In the next step, the user is prompted via the LC display 6 to enter the test subject's body weight, if a metering mode related to the body weight was selected, and a preset value of, e.g., 65 kg, is first displayed, which can be increased or decreased by actuating the adjusting member 23, and it is finally read into the control device 4 by depressing the adjusting member 23. A metering rate recommended for the solution 7 to be metered and for the body weight of the test subject is displayed on the LC display 6 in the next step. This metering rate can also be increased or decreased if necessary by means of the adjusting member 23, and it is confirmed by depressing the adjusting member 23, i.e., by acknowledgement. The metering system 1 then passes over to standby function, and further channels can be defined in the same manner if necessary.

To start or regulate metering, the channel containing the solution 7 to be metered is first selected, i.e., the selector switch 13 for the channel I is depressed, after which the Metering Start key 17 is actuated (FIG. 1 ). If the metering rate is to be changed during the operation, the corresponding channel must first be selected by depressing the selector switch 13, after which the Metering Rate key 19 is depressed, and a new metering rate is set and acknowledged with the adjusting member 23. Metering in the channel selected can be interrupted or further regulated by depressing the Metering Stop key 18.

Besides the automatic metering of the solutions 7 initiated by the control device 4, manually controlled metering of the solutions 7 is also possible, which is performed as follows. After the corresponding fluid flow channel, e.g., the channel I, has been selected with the selector switch 13 belonging to the channel I, and after the manual operating switch 25 has subsequently been actuated, the motor drive 12 belonging to the channel I is brought by a control command sent by the control device 4 into the switched-off position, so that the syringe plunger 11 is displaceable along the arrow 27 by manual pressure (FIG. 1). The flow-measuring means 121 of the channel 1 records the manual displacement of the plunger, and sends corresponding measured signals via the control lines 15 to the control device 4, in which the fluid rate metered is monitored, and corresponding information on this is communicated to the user via the LC display 6. Manual metering thus continues to be switched on as long as the manual operating switch 25 is depressed. When the manual operating switch 25 is released, the motor drive 12 is first switched to standby before automatic metering can again be activated.

Figure 4:
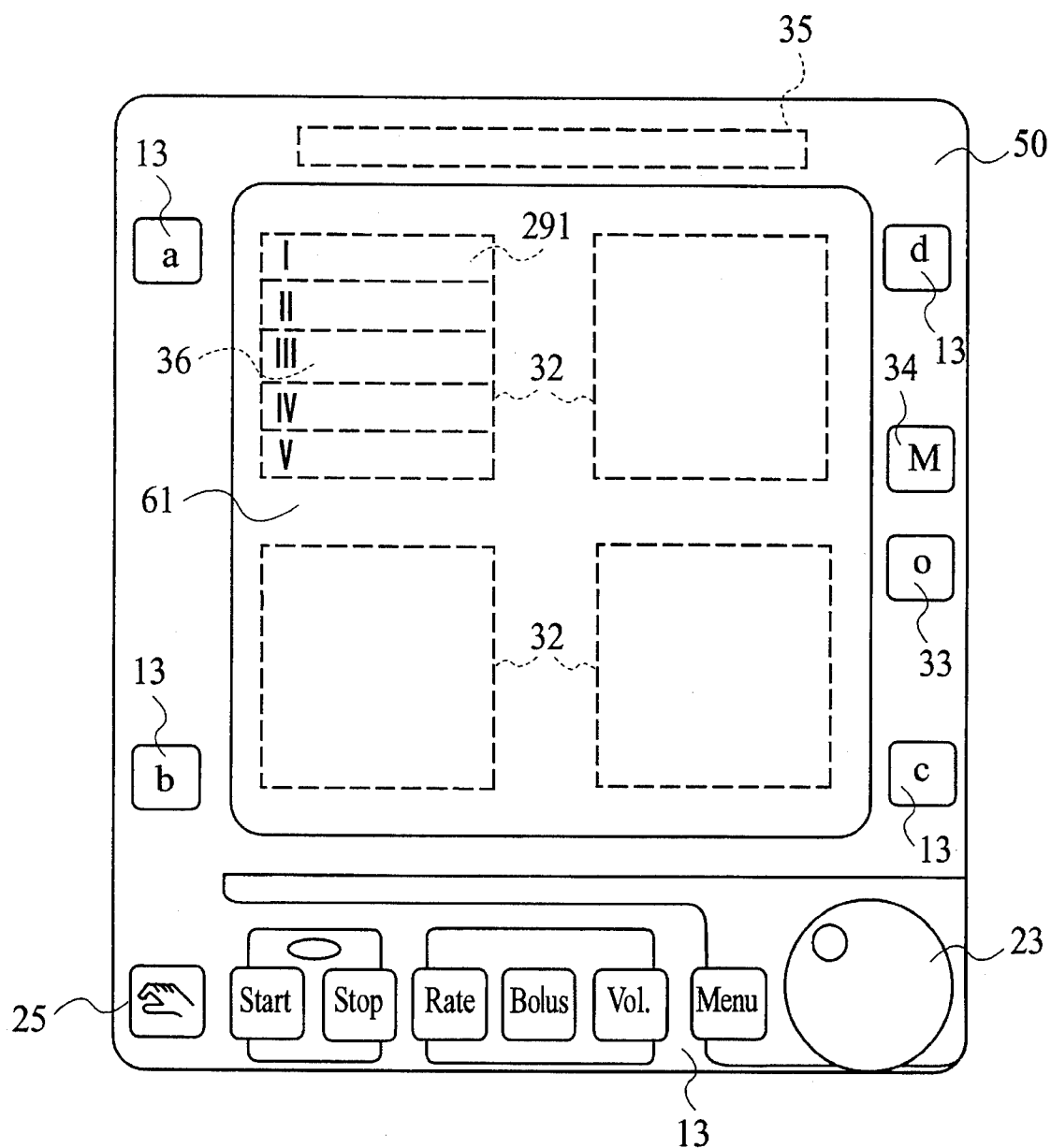
FIG. 4 is an operating surface structured according to fluid flow sources.

FIG. 4 shows the schematic design of a second operating surface 50 of a 20-channel metering system, not shown in the figure, with a display screen 61 as the data output circuit and with a data input 10 with the selector switches 13 and changeover switches 33, 34 belonging to it.

Identical components are designated with the same reference numerals as in FIGS. 1 through 3. The difference from the metering system 1 represented in FIG. 1 is the fact that the selector switches 13, a, b, c, d are assigned here to predetermined groups 32 of the fluid flow sources 3, which are likewise not shown in FIG. 4. The groups 32 are illustrated on the display screen 61 as blocks drawn by broken lines, and a division of channels by Roman numerals I through V is illustrated with display lines 291, which are associated with a defined fluid flow source 3 each, as a representative of the other groups, in the group 32 in the upper left part of the display screen 61.

The groups 32 can either be structured according to the physiological action of the drugs to be metered, or organ-specific groups are formed, so that rapid access to a defined fluid flow source 3 is possible due to the prestructured groups in the case of a change in parameters. Using the changeover switch 33, it is possible to represent an organ-related synoptic diagram on the display screen 61 such that the solutions 7 being metered are directly associated with the organ in question. Switching back to the drug-specific representation, which is illustrated in FIG. 4, is possible by means of the changeover switch 34.

If the metering rate of a defined fluid flow source, e.g., that of the channel II, is to be changed or edited on the second operating surface 50, the corresponding group 32 is first selected by means of the changeover switch 13, a, in the upper left part of the display screen 61. This places the control device in the metering management mode for all flow sources in group 32 and channel II is selected by means of a cursor, which can be influenced via the adjusting member 23, and the selection is acknowledged by depressing the adjusting member 23.

The data field of channel II, which is not shown, is displayed in the field 36 of the upper left group 32 by overwriting the secondary segments in the display lines 291, which secondary segments are associated with the channels and are likewise not represented in FIG. 4, and the metering rate can be set to a new value in the known manner by turning the adjusting member 23. Display devices 35 for warnings, which signal the exceeding of limit values, are provided in tile upper part of the operating surface.

While a specific embodiment of the invention has been shown and described in detail to illustrate the application of the principles of the invention, it will be understood that the invention may be embodied otherwise without departing from such principles.

What is claimed is:

1. Multichannel metering system for metering preselected fluid flows, comprising:

a plurality of individual fluid flow sources;

a plurality of discharge lines, each line of said discharge lines being connected to a corresponding one of said fluid flow sources;

adjusting means associated with said fluid flow sources for acting on said fluid flow sources to influence fluid flow of said fluid flow sources;

programmable control means coupled with said adjusting means for controlling said adjusting means, said programmable control means having data fields describing metering properties of individual fluid flows;

an operating surface connected to said control means;

data input means for input of data into said control means, said data input means being at least partially connected to said operating surface;

data output means for output of data from said control means, said data output means being connected to said operating surface;

selector switch means forming a part of said data input means, said selector switch means including a plurality of selector switches, each selector switch being associated with a set of said fluid flow sources for representing segments of data fields belonging to a corresponding set of fluid flow sources on said operating surface, said each selector switch functionally connecting said data input means with said data fields belonging to said associated set of fluid flow sources.

2. Metering system according to claim 1, wherein said selector switches are arranged in an area immediately adjacent to said fluid flow sources.

3. Metering system according to claim 1, wherein said selector switches are positioned immediately adjacent to said adjusting means.

4. Metering system according to claim 1, further comprising indicator means associated with said selector switch means for indicating a tactile actuation of individual ones of said selector switches.

5. Metering system according to claim 2, further comprising indicator means associated with said selector switch means for indicating a tactile actuation of individual ones of said selector switches.

6. Metering system according to claim 3, further comprising indicator means associated with said selector switch means for indicating a tactile actuation of individual ones of said selector switches.

7. Metering system according to claim 1, further comprising individual display unit means for representing predetermined fluid flow parameters including a display unit associated with each of said selector switches.

8. Metering system according to claim 1, further comprising a manual operating switch for switching off said adjusting means and for manually metering fluid flow.

9. Metering system according to claim 8, wherein said adjusting means is activated by one of said selector switches.

10. Metering system according to claim 1, further comprising flow-measuring means for determining fluid flow being metered into said discharge lines, said flow measuring means being in functional connection with said programmable control means.

11. Metering system according to claim 1, wherein each said data field is divided into individual primary segments and secondary segments, which are related to fluid flow sources, said each selector switch connecting said data input means with said second segments of said associated set of fluid flow sources.

12. Metering system according to claim 11, wherein said data output means includes a display line or a display column, said secondary segments belonging to one fluid flow source being represented in one of said display line and display column.

13. Metering system according to claim 11, wherein said data output means includes a reference field for representing a change in status of at least one of said primary segment and secondary segment, which has been brought into functional connection with said data input means.

14. Metering system according to claim 12, wherein said data output means includes a reference field for representing a change in status of at least one of said primary segment and secondary segment, which has been brought into functional connection with said data input means.

15. Metering system according to claim 11 wherein said programmable control means establishes a status of at least individual parts of said primary segments in a restrictively guided operating sequence predetermined by said programmable control means.

16. A system in accordance with claim 1, wherein:
said set associated with said each selector switch contains only one of said fluid flow sources.

17. Multichannel metering system for metering preselected fluid flows, comprising:
a plurality of individual fluid flow sources;
a plurality of discharge lines, each line of said discharge lines being connected to a corresponding one of said fluid flow sources;
adjusting means associated with said fluid flow sources for acting on said fluid flow sources to influence fluid flow of said fluid flow sources;
programmable control means coupled with said adjusting means for controlling said adjusting means, said programmable control means having data fields describing and metering properties of individual fluid flows;
an operating surface connected to said control means;
data input means for input of data into said control means, said data input means being at least partially connected to said operating surface;
data output means for output of data from said control means, said data output means being connected to said operating surface;
selector switch means associated with a predetermined group of said fluid flow sources for bringing data fields belonging to said predetermined group of fluid flow sources to said operating surface; and
separate display units associated with said adjusting means for displaying a predetermined actual value of fluid flow being metered from a corresponding said fluid flow source.

18. Multichannel metering system for metering preselected fluid flows, comprising: a plurality of individual fluid flow sources divided into a plurality of sets; a plurality of discharge lines, each line of said discharge lines being connected to a corresponding one of said fluid flow sources;
adjusting means associated with said fluid flow sources for acting on said fluid flow sources to influence fluid flow of said fluid flow sources;
control means coupled with said adjusting means for controlling said adjusting means, said control means having data fields describing said fluid flow sources and metering parameters of said individual fluid flows, said control means including a meter management mode for editing and regulating said metering parameters;
a operating surface connected to said control means;
data input means for input of data into said control means, said data input means being at least partially connected to said operating surface;
data output means for output of data from said control means, said data output means being connected to said operating surface;
a plurality of selector switch means, each of said selector switch means being associated with one of said plurality of sets of said fluid flow sources, said each selector switch means placing said control means in said meter management mode for said associated set of fluid flow sources.

19. A system in accordance with claim 18, wherein:
each of said associated sets of fluid flow sources contain only one fluid flow.

20. A system in accordance with claim 18, wherein:
said input data means is a singular unit and is connected by said each selector switch to said metering parameters of said associated set of fluid source flows.

* * * * *